US007265097B2

(12) United States Patent  
Kydonieus et al.

(10) Patent No.: US 7,265,097 B2  
(45) Date of Patent: Sep. 4, 2007

(54) METHODS OF DRUG DELIVERY USING SULPHATED CHITINOUS POLYMERS

(75) Inventors: Agis Kydonieus, Kendell Park, NJ (US); Clive Elson, Halifax (CA); Maya Thanou, Thessaloniki (GR)

(73) Assignee: Chitogenics, Inc., Chatham, NJ (US)

( * ) Notice: Subject to any disclaimer, the term of this patent is extended or adjusted under 35 U.S.C. 154(b) by 508 days.

(21) Appl. No.: 10/224,173

(22) Filed: Aug. 20, 2002

(65) Prior Publication Data

US 2004/0038870 A1 Feb. 26, 2004

(51) Int. Cl.
*A01N 43/04* (2006.01)
*A01N 61/00* (2006.01)

(52) U.S. Cl. .......................................... 514/55; 514/1

(58) Field of Classification Search .................. 514/24, 514/1, 2, 44, 55; 536/20
See application file for complete search history.

(56) References Cited

U.S. PATENT DOCUMENTS

| | | | |
|---|---|---|---|
| 4,141,973 A | 2/1979 | Balazs ........................ 424/180 |
| 4,424,346 A | 1/1984 | Hall et al. .................... 536/20 |
| 4,570,629 A | 2/1986 | Widra ......................... 128/156 |
| 4,619,995 A | 10/1986 | Hayes ......................... 536/20 |
| 4,659,700 A | 4/1987 | Jackson ....................... 514/55 |
| 4,819,617 A | 4/1989 | Goldberg et al. ........... 128/897 |
| 4,868,113 A | 9/1989 | Jaye et al. ................... 435/70 |
| 4,886,787 A | 12/1989 | de Belder et al. ............ 514/57 |
| RE33,375 E | 10/1990 | Luck et al. ..................... 514/2 |
| 4,978,332 A | 12/1990 | Luck et al. .................. 604/19 |
| 5,023,090 A | 6/1991 | Levin ......................... 424/520 |
| 5,080,893 A | 1/1992 | Goldberg et al. ............. 514/57 |
| 5,093,319 A | 3/1992 | Higham et al. ............... 514/55 |
| 5,140,016 A | 8/1992 | Goldberg et al. ............. 514/57 |
| 5,234,915 A | 8/1993 | Mathur et al. ................ 514/57 |
| 5,411,988 A | 5/1995 | Bockow et al. ............. 514/560 |
| 5,412,084 A | 5/1995 | Elson et al. ................... 536/20 |
| 5,460,939 A | 10/1995 | Hansbrough et al. ........ 435/1.1 |
| 5,462,990 A | 10/1995 | Hubbell et al. ............. 525/54.1 |
| 5,470,829 A | 11/1995 | Prisell et al. ................. 514/12 |
| 5,474,765 A * | 12/1995 | Thorpe ..................... 424/78.17 |
| 5,510,102 A | 4/1996 | Cochrum ................. 424/78.08 |
| 5,679,658 A | 10/1997 | Elson .......................... 514/55 |
| 2003/0219479 A1* | 11/2003 | Chen et al. .................. 424/466 |

FOREIGN PATENT DOCUMENTS

| | | |
|---|---|---|
| EP | 312 208 A1 | 4/1989 |
| EP | 368 253 A2 | 5/1990 |
| EP | 637 450 A2 | 2/1995 |
| EP | 650 999 A1 | 5/1995 |
| EP | 665 022 A1 | 8/1995 |
| EP | 1095650 A1 | 5/2001 |
| WO | WO89/05646 A1 | 6/1989 |
| WO | WO93/13137 A1 | 7/1993 |
| WO | WO96/13282 A1 | 5/1996 |
| WO | WO96/13284 A1 | 5/1996 |

OTHER PUBLICATIONS

Tokura et al (J.M.S. Pure Appl. Chem. A31(11): 1701-1718, 1994).*
Kratz et al (Scand. J. Plastic Recon. Surg. Hand Surg. 31(2): 119-123, 1997).*
Holme et al (Carbohydrate Res. 302:7-12, 1997).*
van der Lubben et al (Eur. J. Pharm. Sci. 14 : 201-207, 2001).*
Natsume et al (International journal of pharmaceutics, (Aug. 5, 1999) 185 (1) 1-12).*
Thanou et al (Pharm. Res. 17(1): 27-31, 2000).*
Brayden, D. et al. "Heparin absorption across the intestine: Effects of sodium N-[8-(2-hydroxybenzoyl)amino]caprylate in rat in situ intestinal instillations and in caco-2 monolayers," *Pharmaceutical research* 14(12):1772-1779 (1997).
Dodane, V. et al. "Pharmaceutical applications of chitosan," *Pharm. Sci. Techn. Today* 1998;1:246-253.
Dodane, V. et al. "Effect of chitosan on epithelial permeability and structure," *Int. J. Pharm.* May 10, 1999;182(1):21-32.
Hirano, S. et al. "Effect of sulfated derivatives of chitosan on some blood coagulant factors," *Carbohydrate Research* 137:205-215 (1985).
Illum, L. "Chitosan and its use as a pharmaceutical excipient," *Pharm. Res.* Sep. 1998;15(9):1326-31.
Illum, L. et al. "Chitosan as a novel nasal delivery system for peptide drugs," *Pharm. Res.* Aug. 1994;11(8):1186-9.
Leone-Bay, A. et al. "Synthesis and evaluation of compounds that facilitate the gastrointestinal absorption of heparin," *J. Med. Chem.* 41:1163-1171 (1998).
Muzzarelli, R.A.A. et al. "Sulfated N-(carboxymethyl)chitosans: novel blood anticoagulants," *Carbohydrate Res.* 126(2):225-231 (1984).
Thanou, M. et al. "Intestinal absorption of octreotide: N-trimethyl chitosan chloride (TMC) ameliorates the permeability and absorption properties of the somatostatin analogue in vitro and in vivo," *J. Pharm. Sci.* Jul. 2000;89(7):951-7.
Thanou, M. et al. "N-trimethylated chitosan chloride (TMC) improves the intestinal permeation of the peptide drug buserelin in vitro (Caco-2 cells) and in vivo (rats)," *Pharm. Res.* Jan. 2000;17(1):27-31.

(Continued)

*Primary Examiner*—Richard Schnizer
(74) *Attorney, Agent, or Firm*—Ralph Loren; Edwards Angell Palmer and Dodge (57) ABSTRACT

The present invention provides methods and compositions for delivering a therapeutic agent across a membrane that has limited permeability for the therapeutic agent. The method includes delivering the therapeutic agent to the membrane in a composition which includes a sulphated chitinous polymer as a primary carrier.

18 Claims, 3 Drawing Sheets

OTHER PUBLICATIONS

Thanou, M. et al. "Effect of degree of quaternization of N-trimethyl chitosan chloride for enhanced transport of hydrophillic compounds across intestinal caco-2 cell monolayers," *J. Control Release.* Feb. 14, 2000;64(1-3):15-25.

Thanou, M. et al. "Effect of N-trimethyl chitosan chloride, a novel absorption enhancer, on caco-2 intestinal epithelia and the ciliary beat frequency of chicken embryo trachea," *Int. J. Pharm.* Aug. 5, 1999;185(1):73-82.

Thanou, M. "Mono-N-carboxymethyl chitosan (MCC)" Thesis, chapter 9, pp. 138-152, no date.

Tokura, S. et al. "Selective sulfation of chitin derivatives for biomedical functions," *J.M.S. Pure Appl. Chem.* A31(11):1701-1718 (1994).

Whistler, R.L. et al. "Anticoagulant activity of oxidized and *N*- and O-sulfated chitosan," *Arch. Biochem. Biophys.* 142:106-110 (1971).

\* cited by examiner

METHODS OF DRUG DELIVERY USING SULPHATED CHITINOUS POLYMERS

BACKGROUND OF THE INVENTION

Chitin (N-acetyl glucosamine) is a naturally occurring polysaccharide and many of its derivatives, including chitosan, have applications in the biomedical field. Chitosan is a deacetylated chitin derivative and includes a variety of polymers with different degrees of deacetlyation and depolymerization. Most chitosans are soluble at pHs below 7 and many form hydrogels when dissolved in aqueous solutions.

Over the last decade, chitin and its derivatives have become the focus of interest in biomedical and biopharmaceutical research. As a biocompatible polymer, chitosan has been used for a variety of applications as a biomaterial for tissue engineering, wound healing, and as an excipient for drug delivery. Chitosan can be used as a drug delivery agent for a wide variety of therapeutics. For example, DNA complexation with chitosan yields suitable nano- and microparticulate formulations for transfection in vivo and in vitro. In addition, peptide and protein delivery using chitosan as functional carriers has also been reported.

However, at neutral and basic pHs, underivatized chitosan aggregates and precipitates out of solution. This has limited the applications of underivatized chitosans, in oral drug delivery, due to the neutral to alkaline environment of the intestinal tract.

Accordingly, it is an object of the invention to provide a method for delivering a therapeutic agent across a membrane that has limited permeability for the therapeutic agent. The therapeutic agent is provided to the membrane in a composition that includes a sulphated chitinous polymer.

It is also an object of the invention to provide a method for treating a subject with a therapeutic agent by administering the therapeutic agent to the subject in a composition having a sulphated chitinous polymer as a primary carrier.

These and other objects, features, and advantages of the invention will be apparent from the following description and claims.

SUMMARY OF THE INVENTION

The present invention provides a method for delivering a therapeutic agent across a membrane that has limited permeability for the therapeutic agent. The method includes delivering the therapeutic agent to the membrane in a composition which includes a sulphated chitinous polymer as a primary carrier.

The present invention is particularly well adapted for membranes such as those composed of epithelial cells or endothelial cells. The membrane may be located on a subject's nose, stomach, mouth, intestine, vagina, skin or eye. The method and composition are useful for delivering a broad variety of therapeutic agents. The therapeutic agents may include proteins, peptides, nucleic acids, or fragments thereof. Preferred peptides have a molecular weight of between about 700 to about 5000 daltons, while preferred proteins have a molecular weight between about 5000 and 500,000 daltons. The invention is also useful with small molecules or compounds having a molecular weight between about 100 to about 700 daltons.

Sulphated chitinous polymers useful in the invention preferably have a degree of sulphation between about 0.03 and about 1.0. In some circumstances, degrees of sulphation are between about 0.1 and about 1.0, between about 0.1 and about 0.6, or between about 0.2 and about 0.4 may be used. Such materials can be prepared by sulphation of chitosan or a carboxymethylchitosan and have molecular weights that range from 10,000 to 3 million daltons. The starting chitosan can be deacetylated from 30 to 100% and the degree of carboxymethylation can vary between 30 and 110%.

The composition may include a permeation enhancer, such as a surfactant. Examples of permeation enhancers include, but are not limited to, docusate sodium, docusate calcium, docusate potassium, sodium dodecyl sulfate, sodium caprylate, sodium cholate, sodium deoxycholate, sodium taurocholate, sodium glycocholate, and mixtures thereof. The composition may also include a protecting agent, such as a protease inhibitor, a stabilizing agent, or mixtures thereof.

The invention also provides a method for treating a subject with a therapeutic agent by delivering the therapeutic agent across a membrane which has limited permeability for the therapeutic agent. The method includes administering a composition to the subject which includes the therapeutic agent and a sulphated chitinous polymer as a primary carrier. The composition may be administered to the subject orally.

The invention also provides a pharmaceutical composition comprising a sulphated chitinous polymer and a therapeutic agent. The pharmaceutical composition may also include a protecting agent.

DETAILED DESCRIPTION OF THE INVENTION

The invention is directed to methods and compositions for delivering therapeutic agents and other macromolecules across membranes having limited permeability for those compounds, using a composition which includes sulphated chitinous polymer(s) as a primary carrier. The sulphated chitinous polymers allow the therapeutic agent to permeate through the membrane and be absorbed systemically by the subject.

Mucosal membranes fall into the class of membranes that have limited permeability to therapeutic agents, especially those of molecular weight above 500 daltons which includes most peptides and proteins. These membranes are generally characterized by a lining of epithelial or endothelial cells having "tight junctions" that physiologically connect the enterocytes apically. Examples of such membranes are located in or on the skin, ear, eye, nose, gastrointestinal tract (e.g., mouth, throat, esophagus, stomach, large intestine, small intestine, etc.), reproductive tract (e.g., vagina, uterus, etc.), of a subject.

Examples of subjects include mammals, such as dogs, pigs, sheep, cows, cats, horses, goats, ferrets, mice, rats, rabbits, bears, monkeys, gorillas, chimpanzees, and, preferably, humans.

The term "primary carrier" is meant to describe the fact that the sulphated chitinous polymer allows the composition to perform its intended function, e.g., deliver the therapeutic agent across a membrane that would normally not be permeable to it. The composition may have between about 0.01% to about 99.9% of the sulphated chitinous polymer, by weight, and still have the sulphated chitinous polymer as the "primary carrier." Preferred liquid compositions have the primary carrier as between about 0.1% to about 50%, between about 0.1% to about 25%, or between about 1.0% and about 10%, by weight, of the total composition.

The term "sulphated chitinous polymers" includes sulphated derivatives of chitin and chitosan. Examples of chitinous polymers include those described in, for example, in Tokura et al. *J. M. S.—Pure Appl. Chem.* A31 (11), pp. 1701-1718 (1994); Hirano et al. *Carbohydrate Research*, 137 (1985) p. 205-215; and Whistler et al. *Archives Biochem. Biophys.* 142 (1971) p. 106-110, hereby incorporated herein by reference in their entirety. Examples of primary carriers include sulphated chitinous polymers, such as N-sulphated- N,O-carboxymethylchitosan, N-sulphated O-carboxymethylchitosan, and sulphated chitosan.

The sulphated chitinous polymers may be synthesized by using methods known in the art. For example, generally, NOCC has about 30-70% of the total nitrogen centers on the polymer in the form of amines. The amines may then react with a sulfur trioxide-pyridine reagent at room temperature and basic pH to form NHSO$_3$ groups along the polymer. The oxygen centers in chitosan and its derivatives can also be sulphated under anhydrous conditions using dimethylformamide—sulfur trioxide reagents. It is expected that O-sulphated or N,O-sulphated chitinous materials will also perform in accordance with the teachings of this invention.

Idealized structures of each of these sulphated chitinous polymers are shown below. These structures are not meant to be limiting, with respect to the derivatization of the chitinous polymer. One of skill in the art will appreciate that the derivatization pattern of the polymers and/or the particular salt can be varied, as appropriate.

Sulphated Chitosan (S-SAN)

N-Sulphated N,O-Carboxymethyl Chitosan (S-NOCC)

N-Sulphated O-Carboxymethyl Chitosan (S-OCC)

The term "therapeutic agent" includes low molecular weight drugs, proteins, peptides, oligonucleotides, nucleic acids, polysaccharides and other macromolecules. It includes agents which can be transported across the membrane using the permeation enhancing sulphated chitinous polymers of the invention.

The term "drugs" includes small molecules, such as organic compounds, with a molecular weight of between about 50 and about 1000 daltons. More preferably the compounds have a molecular weight between about 100 daltons and about 700 daltons.

The term "peptide" includes therapeutic agents with a molecular weight between about 700 to about 5000 daltons. Like the proteins, the peptides may be naturally occurring, recombinant or chemically synthesized.

The term "proteins" include therapeutic agents with a molecular weight between about 5000 and about 500,000 daltons, or between about 5000 and about 150,000 daltons. The proteins may be naturally occurring, recombinant or chemically synthesized.

The term "therapeutic macromolecule" means any macromolecule that provides a therapeutic effecting, includes mucopolysaccharides or glycosaminoglycans such as heparin.

Examples of peptides and proteins include, for example, cytokines, peptide hormones, growth factors, cardiovascular system factors, cell adhesion factors, central and peripheral nervous system factors, humoral factors, bone and skeleton factors, gastrointestinal system factors, kidney and urinary organ factors, connective tissue and skin factors, sense organs factors, immune system factors, respiratory system factors, genital organ factors, enzymes, and fragments and portions thereof.

The cytokines include lymphokines (e.g., interferons (e.g., interferon-α, -β and -γ), interleukins (e.g. interleukin 2 through 11), monokines (e.g., interleukin-1)), tumor necrosis factors (e.g. TNF-α and -β), malignant leukocyte inhibitory factor (LIF), and hematopoietic factors (e.g., erythropoietin), granulocyte colony stimulating factor (G-CSF), granulocyte-macrophage stimulating factor (GM-CSF), macrophage colony stimulating factor (M-CSF), and fragments and analogs thereof.

Examples of bone and skeleton factors include bone GLa peptide, parathyroid hormone and its active fragments (osteostatin, *Endocrinology* 129:324, 1991), histone H4-related bone formation and proliferation peptide (OGP, EMBO 11: 1867, 1992), and fragments and analogs thereof.

Examples of growth factors include nerve growth factors (NGF, NGF-2/NT-3), epidermal growth factor (EGF), fibroblast growth factor (FGF), insulin-like growth factor (IGF), transforming growth factor (TGF), platelet-derived cell growth factor (PDGF), hepatocyte growth factor (HGF), and fragments and analogs thereof.

Examples of peptide hormones include insulin, growth hormone, luteinizing hormone-releasing hormone (LHRH), adrenocorticotropic hormone (ACTH), amylin, oxytocin, luteinizing hormone and other factors acting on the genital organs, and fragments and analogs thereof.

Examples of cardiovascular system factors include factors which modulate blood pressure, arteriosclerosis, etc. These factors include endothelins, endothelin inhibitors, endothelin antagonists, endothelin producing enzyme inhibitors, vasoppressin, renin, angiotensin I, angiotensin II, angiotensin III, angiotensin I inhibitor, angiotensin II receptor antagonist, atrial naturiuretic peptide (ANP), antiarrythmic peptide, and fragments and analogs thereof.

Examples of central and peripheral nervous system factors include opioid peptides (e.g. enkephalins, endorphins, kyotorphins), neurotropic factor (NTF), calcitonin gene-related peptide (CGRP), thyroid hormone releasing hormone (TRH), neurotensin, and fragments and analogs thereof.

Examples of gastrointestinal system factors are secretin and gastrin. Examples of humoral factors include calcitonin, apoprotein E and hirudin and other factors which modulate hemagglutination, plasma cholesterol level or metal ion concentrations. Examples of the cell adhesion factors include laminin and intercellular adhesion molecule 1 (ICAM 1). Examples of kidney and urinary tract factors include naturiuretic peptide (BNP), urotensin, and fragments and analogs thereof. Examples of immune system factors include chemotactic peptides and bradykinins.

The compositions of the invention may include a secondary permeation enhancer, such as a surfactant. These permeation enhancers include, but are not limited to, docusate sodium, docusate calcium, docusate potassium, sodium dodecyl sulfate, sodium caprylate, sodium cholate, sodium deoxycholate, sodium taurocholate, sodium glycocholate, and mixtures thereof. Similarly, the composition may also include a protecting agent, such as a protease inhibitor like tetracycline, a stabilizing agent, or mixtures thereof.

The compositions of the invention may also include an additional pharmaceutically acceptable carrier. The additional pharmaceutical acceptable carrier is generally administered to the subject in combination with the primary carrier and the therapeutic agent.

The additional pharmaceutically acceptable carrier may include a pharmaceutically acceptable material, composition or vehicle, such as a liquid or solid filler, diluent, excipient, solvent or encapsulating material, involved in carrying or transporting the therapeutic composition of the invention, e.g., a therapeutic agent and a sulphated chitinous polymer, within or to the subject such that the composition can perform its intended function, e.g., deliver the therapeutic agent across a membrane. Such compositions are generally carried or transported from one organ, or portion of the body, to another organ, or portion of the body. Each additional carrier must be "acceptable" in the sense of being compatible with the other ingredients of the formulation and not injurious to the subject. Some examples of materials which can serve as additional pharmaceutically acceptable carriers include: water; sugars such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The sulphated chitinous polymers generally contain basic functional groups, such as amino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the invention. These salts can be prepared in situ during the final isolation and purification of the compounds of the invention, or by separately reacting a purified compound of the invention in its free base form with a suitable organic or inorganic acid, and isolating the salt thus formed. Representative salts include hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al (1977) "Pharmaceutical Salts", *J. Pharm. Sci.* 66:1-19).

The sulphated chitinous polymers may also contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the invention. These salts can likewise be prepared in situ during the final isolation and purification of the compounds, or by separately reacting the purified compound in its free acid form with a suitable base, such as hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants may also be present in the composition of the invention.

Formulations of the invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The formulations may include, but are not limited to, the therapeutic agent, the sulphated chitinous polymer, and an additional pharmaceutically acceptable carrier.

Formulations of the invention suitable for oral administration may be in the form of capsules, cachets, pills, enteric-coated tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the therapeutic agent. The formulations of the invention may also be administered as a bolus, electuary or paste.

In solid dosage forms of the invention for oral administration (capsules, tablets, pills, dragees, powders, granules and the like), the therapeutic agent and sulphated chitinous polymer are mixed with one or more additional pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrate (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the compositions of the invention, such as dragees, capsules, pills and granules, may optionally be scored or prepared with coatings and shells, such as enteric coatings and other coatings well known in the pharmaceutical-formulating art. They may also be formulated so as to provide slow or controlled release of the therapeutic agent and sulphated chitinous polymer therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes.

Liquid dosage forms for oral administration of the therapeutic agents and sulphated chitinous polymer include pharmaceutically acceptable emulsions, microemulsions, solutions, suspensions, syrups and elixirs. In addition to the sulphated chitinous polymer and therapeutic agent, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the therapeutic agent and sulphated chitinous polymer, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the therapeutic agent and sulphated chitinous polymer for rectal or vaginal administration may be presented as a suppository, which may be prepared by mixing the therapeutic agent and the sulphated chitinous polymer with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the therapeutic agent and sulphated chitinous polymer. Formulations of the invention which are suitable for vaginal administration also include pessaries, tampons, creams, gels, pastes, foams or spray formulations containing such carriers as are known in the art to be appropriate.

Dosage forms for the topical or transdermal administration of a therapeutic agent and sulphated chitinous polymer of this invention include powders, sprays, ointments, pastes, creams, lotions, gels, solutions, and patches. The therapeutic agent and sulphated chitinous polymer may be mixed under sterile conditions with a pharmaceutically acceptable carrier, and with any preservatives, buffers, or propellants which may be required.

The ointments, pastes, creams and gels may contain, in addition to the therapeutic agent and sulphated chitinous polymer, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Transdermal patches have the added advantage of providing controlled delivery of a compound to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise a therapeutic agent and sulphated chitinous polymer in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. The invention also provides a pharmaceutical composition comprising a sulphated chitinous polymer, and a therapeutic agent. The therapeutic agent may also include a protecting agent or a additional pharmaceutically acceptable carrier.

The invention is further explained by the following examples.

EXAMPLE 1

Influence of S-NOCCs on the TEER and Viability of the Caco-2 Cells.

This example demonstrates the ability of sulphated chitinous polymers to enhance the permeability through intestinal epithelial cells. The Caco-2 intestinal epithelial cells used in this example form apically tight junctions that seal the paracellular pathways. Disruption of the tight junctions' barrier leads to increased paracellular permeability of hydrophilic drugs that are poorly absorbed across the intestine. The integrity of the tight junctions can be determined by measuring decreases in the transepithelial electrical resistance (TEER) when the tight junctions are opened.

Caco-2 cell cultures were seeded initially from cryovials (stored in liquid nitrogen) to flasks and treated with trypsin. After trypsin treatment, cells were seeded on the Costar Transwell filters (24-well plates, Costar Europe, Badhoevedorp, The Netherlands) at a seeding density of $10^4$ cells/cm$^2$. Dulbecco's Modified Eagle's Medium (DMEM, Sigma, Bornem; Belgium; pH=7.4), supplemented with 1% nonessential amino acids, 10%, fetal calf serum (Hyclone, Greiner, The Netherlands), benzyl-penicillin G (160 U/ml) and streptomycin sulfate (100 µg/ml) (Sigma) was used as culture medium, and was added to both the donor and the acceptor compartment. The medium was changed every second day. The cell cultures were kept at a temperature of 37° C., in a humidified atmosphere of 5% $CO_2$ and 95% air. For the experiments, cells were used at 21 or 25 days after seeding. The initial transepithelial electrical resistance (TEER) values were 1200 $\Omega cm^2$. Four hours before application of the sulphated chitinous polymers, the medium was replaced by DMEM buffered to pH 7.4 with 40 mM n-(2-hydroxyethyl) piperazine-N-(2-ethanosulfonic acid) (HEPES, Sigma, Bornem, Belgium). Cells with DMEM-HEPES medium served as control.

S-OCC(N-sulphated O-carboxymethyl chitosan), S-NOCC(N-sulphated N,O-carboxymethyl chitosan), and S-SAN (N-sulphated chitosan) were applied on the Caco-2 cell cultures and TEER was measured for 4 hours. After four hours, the polymers were removed. The TEER was also recorded at 24 hrs after application to investigate the viability of the monolayers.

Figure 1:
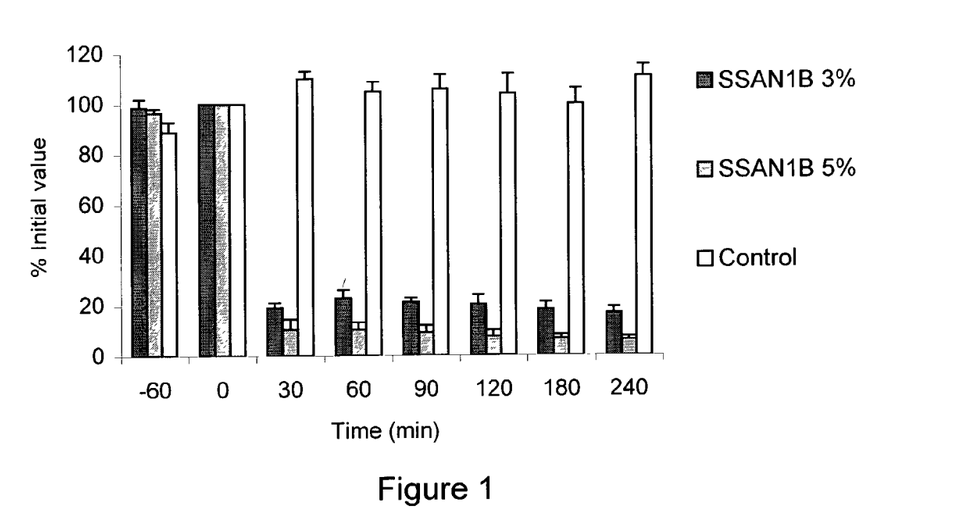
FIG. 1 is a bar graph depicting the trans-epithelial electric resistance (TEER) of Caco-2 cells treated with S-SAN (N-sulphated chitosan).

S-SAN was tested at concentrations of both 3% and 5%. The results of this experiment are depicted in FIG. 1. It was found that at a concentration of 3%, the TEER was about 20% of its initial value over the entire four hour period. At a concentration of 5%, the TEER was about 10% of its initial value for the four hour period. This shows that S-SAN was effective in opening the tight junctions of the epithelial cells.

Figure 2:
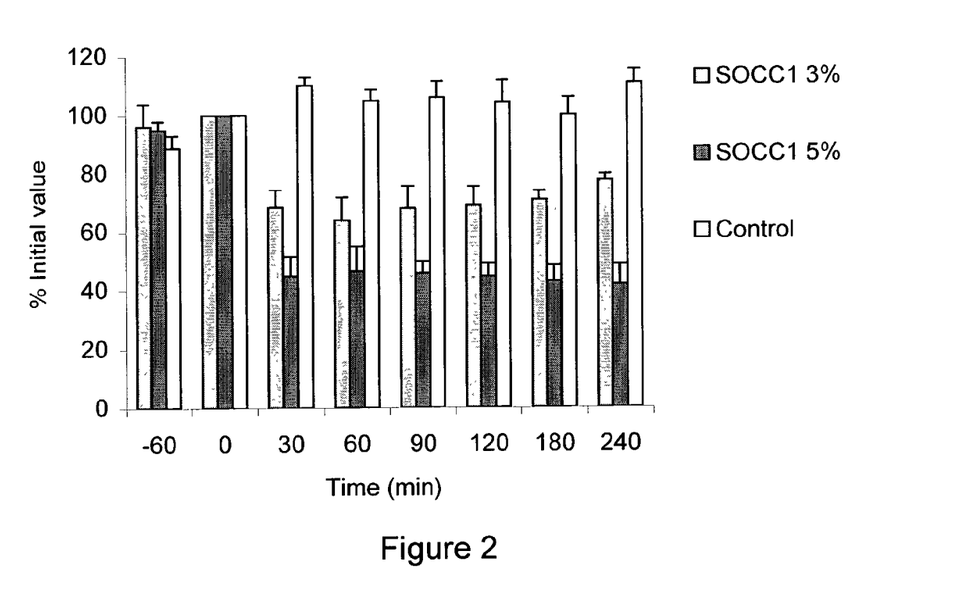
FIG. 2 is a bar graph depicting the TEER of Caco-2 cells treated with S-OCC (N-sulphated O-carboxymethyl chitosan).

S-OCC was also tested at concentrations of both 3% and 5%. The results of this experiment are shown in FIG. 2. It was found that at a concentration of 3%, the TEER was between 60% and 80% of the initial value for the four hour period after application. At the 5% concentration, the TEER was about 40% of the initial measurement throughout the experiment.

S-NOCC was tested at a concentration of 1%. It was found that at this concentration, S-NOCC decreased the TEER to about 80% of its original value for about 4 hours after application.

This example shows that the sulphated chitinous polymers, S-SAN, S-OCC, and S-NOCC, were each able to effectively disrupt the tight junctions between Caco-2 epithelial cells.

EXAMPLE 2

Effect of S-NOCCs as Primary Carriers of LMWH In Vivo

The effect of S-NOCCs (N-sulphated N,O-carboxymethyl chitosans) as primary carriers in vivo was tested using rats. Male Wistar rats (SPF status, approximately 250 g) were obtained from Charles River (NL). The animals were fasted for 16 hours before administration with free access to water. The animals were anesthetized with Hypnorm (fentanyl citrate) and Dormicum (midazolam). The body temperature of the rats was kept at 36-37° C. and was monitored throughout the experiment.

Reviparin LMWH (Reviparin, Knoll, 108 Anti-XaU/mg) solution was prepared in physiological saline at 625 anti Xa U/ml.

S-NOCC was tested at two viscosities 40 and 60 cps (S-NOCC40 and S-NOCC60), representing a lower and higher molecular weight chitinous polymer respectively.

The S-NOCCs were dissolved at 3% (w/v) in the reviparin solution to form a viscous gel.

In order to administer the LMWH formulations, a thin Teflon tube (~1 mm i.d.) was used for the control (no polymer). In order to administer the S-NOCC formulations, a polypropylene tube with i.d. ~3 mm was used to facilitate the viscous gels for their administration. Both tubes were connected to a syringe.

The abdomen of the animals was opened by an incision and the stomach was moved towards the incision point. A small incision at the stomach was made to allow each tube to be guided via the pylorus to the beginning of the duodenum (first 2-3 cm.). Formulation were administered slowly over 5 min and at +/− 2 ml normalized for the body weight of each animal to assure administration of 5000 Anti-Xa U/kg.

Blood samples, ~225 µl, were collected from the tail vein capillaries (after incision) in Eppendorf vials containing 25 µl sodium citrate 3.8%. The samples were centrifuged at 13000 rpm for 20 min.

Analysis of samples was performed using the Chromostrate heparin Anti-Xa assay (Organon Teknika, NL). This assay measures the potentiating effect of Heparin on anti-Xa activity in plasma and medium samples by an amidolytic method using a synthetic chromogenic substrate ($CH_3OCO$-D-Val-Gly-Arg-pNA.AcOH). Samples containing heparin were incubated in the presence of anti-thrombin III (ATIII; plasma cofactor) with an excess of factor Xa forming an ATIII-Heparin-Xa complex. The remaining Xa catalyzed the release of p-nitroaniline (pNA) from the chromogenic substrate. The release of pNA was measured by an end-point method at 405 nm in an EL808 ultra microplate reader (Biotek Instruments Inc.). Analysis of LMWH was performed using a standard calibration curve at the range of 0.0-0.7 Anti Xa Units/ml.

Figure 3:
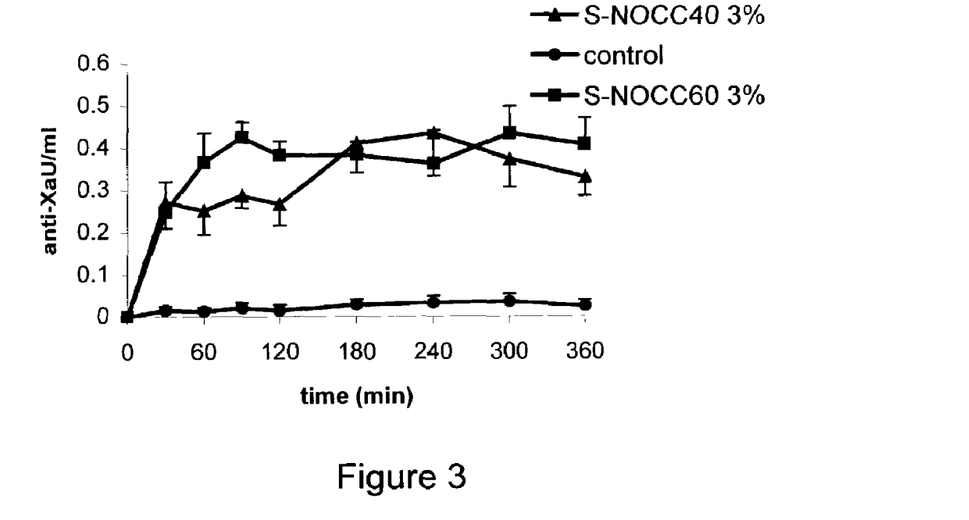
FIG. 3 is a line graph showing the intestinal absorption of LMWH Reviparin in rats when administered with and without S-NOCC(N-sulphated N,O-carboxymethyl chitosan).

FIG. 3 is a graph showing the intestinal absorption of LMWH Reviparin in rats when administered at a dose of 5000 Anti-XaU/kg with or without the sulphated chitinous polymers (for all groups n=6±SEM). Without the S-NOCC polymers, the intestinal absorption of LMWH was limited. The S-NOCCs increased the absorption of the LMWH at and above the antithrombotic levels (0.2 Anti-Xa U/ml). The absorption was sustained throughout the experiment for 6 hours. No major differences were observed between S-NOCC40 and S-NOCC60.

EXAMPLE 3

Effect of S-NOCC on the Transport of $^{14}C$-mannitol Across Caco-2 Cell Monolayers In the presence of a sulphated chitinous polymer, $^{14}C$-mannitol transport across Caco-2 cell monolayers is a quantitative measure of the paracellular enhancement. $^{14}C$-mannitol is an inert, radioactive, uncharged molecule which functions as a marker of the paracellular permeability.

$^{14}C$-Mannitol (MW 182.2; specific radioactivity 57 mCi/mmol) was obtained from Amersham-Pharmacia (The Netherlands). S-NOCC60 was dissolved at concentrations of 1%, 3%, and 5% (w/v) in DMEM-HEPES containing $^{14}C$-mannitol. The pH of the solutions were then adjusted to 7.40. Samples of 200 µl were taken from the basolateral side for 4 hours and were replaced with an equal volume of pre-warmed DMEM-HEPES. Control experiments were run in every experiment with solutions containing the radioactive markers without any dissolved polymers. The radioactivity applied to the cells was determined in 200 µl samples of the solutions tested and background radioactivity was determined in 200 µl samples of DMEM-HEPES without the radioactive marker. The radioactivity present in the samples was determined after adding 3 ml scintillation cocktail (Ultima Gold) in a liquid scintillation counter. Results were corrected for dilution and expressed as cumulative transport at time t.

The transport of mannitol was expressed as $P_{app}$ (apparent permeability co-efficient) calculated according to the following formula:

$$P_{app}=(dC/dt)*(1/A*60* C_0)$$

wherein $P_{app}$ is measured in cm/s, dC/dt is the permeability rate, A is the diffusion area of the monolayer ($cm^2$) and $C_0$ is the initial concentration of the radiomarker.

The enhancement ratios (R) were calculated according the formula:

$$R=P_{app\ polymer}/P_{app\ control}$$

The enhancement ratios and apparent permeability coefficients for each of concentration of S-NOCC60 tested are shown in Table 1 below:

TABLE 1

|  | $P_{app} \times 10^{-8}$ | R |
| --- | --- | --- |
| Control | 4.1 ± 0.8 | 1 |
| S-NOCC60 1% (w/v) | 7.1 ± 8.5 | 1.7 |
| S-NOCC60 3% (w/v) | 61.1 ± 5.8 | 14.8 |
| S-NOCC60 5% (w/v) | 131 ± 15.5 | 28.5 |

At each concentration tested, S-NOCC60 was an efficient permeation enhancer as tested in Caco-2 cell monolayers. The effect on the paracellular permeation appeared to be concentration dependent.

EXAMPLE 4

Effect of S-NOCC60 on the Transport of FD-4 across Caco-2 Cell Monolayers

This example demonstrates the ability of a sulphated chitinous polymer, S-NOCC60, to enhance the permeability of FITC-Dextran (FD-4) through Caco-2 cell monolayers.

The FD-4 (MW 4000, Sigma) solution was prepared in HBSS-HEPES (Hank's Balanced Salt Solution-w/o phenol red, Sigma) at pH 7.4 and at 1 mg/ml concentration. Solutions of S-NOCC60 at concentrations of 3% and 5% (w/v) were applied to the Caco-2 cell monolayers. Samples of 200 µl were taken from the basolateral side for 4 hours.

Analysis of samples was performed by HPLC Size Exclusion Chromatography (SEC). A Waters 515 HPLC pump, a Waters 474 Scanning Fluorescence detector and a Gilson 234 Autoinjector were used. The column was a PSS Suprema 30 from Polymer Standard Service. The eluent was 15/85 Acetonitrile/$CH_3COONH_4$ 0.05M pH=9.0. The retention time was at 7 minutes; however, chromatograms were run up to 15 minutes to investigate the elution of possible degradation products (MW lower than 4000 Da). Samples for calibration curves were prepared with increasing concentration of FD-4.

Figure 4:
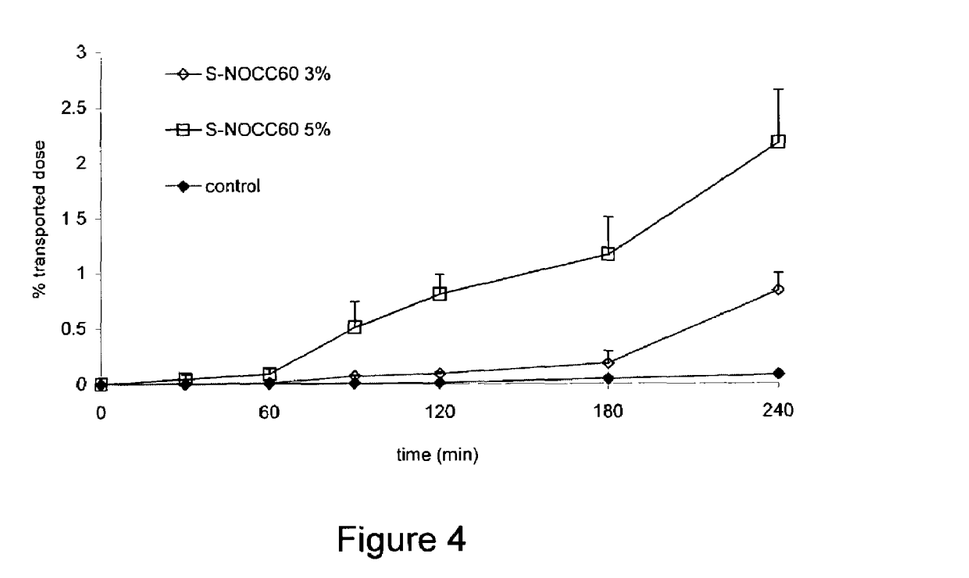
FIG. 4 is a line graph which shows the effect of S-NOCC60 on the transport of FD-4 across Caco-2 cell monolayers.

FIG. 4 is a line graph which shows the effect of S-NOCC60 at 3 and 5% (w/v) on the transport of FD-4 across Caco-2 cell monolayers. The results show that S-NOCC60 substantially increased the permeability of Caco-2 cell monolayers to FD-4.

EXAMPLE 5

Effects of S-NOCC 60, S-SAN, and Sodium Docusate on Insulin Absorbtion In Vivo

In this example, the effect of S-NOCC and SSAN1B with and without sodium docusate was studied using rats. Male Wistar rats (SPF status, approximately 250 g) were obtained from Charles River (NL). The animals were fasted for 16 hours with free access to water. The animals were anesthetized with Hypnorm (fentanyl citrate) and Dormicum (midazolam). Their body temperatures were monitored during operation and throughout the experiment, and were kept at 36-37° C.

A human insulin (Aventis, 25 IU/mg) solution was prepared in physiological saline at 12.5 IU/ml. A second insulin solution was prepared containing docusate at 0.5 mg/ml (~1 mg/rat or 4 mg/kg).

S-NOCC60 and S-SAN were dissolved at 3% (w/v) in the insulin solution and in the docusate insulin solution. Low molecular weight N-substituted carboxymethylchitosan 3% served as control and was tested only with insulin and not in combination with docusate. The insulin was administered to each test animal in a 25 IU/2 ml/rat dose.

Blood samples (~250 µl) were collected from the tail vein capillaries in heparin containing Eppendorf vials. The samples were then centrifuged at 13000 rpm for 20 minutes and the plasma was collected in clean Eppendorf vials. Analysis of plasma samples was performed using Pharmacia Insulin RIA 100 (Pharmacia & Upjohn).

Figure 5:
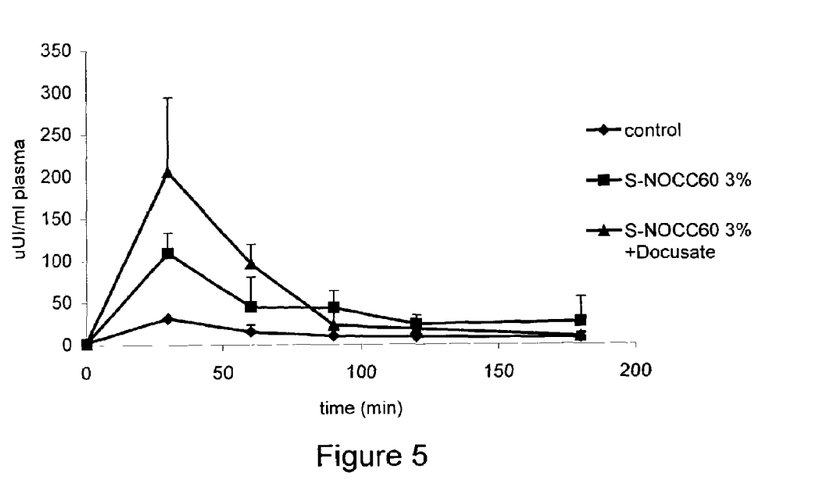
FIG. 5 is a line graph which shows the effect of S-NOCC60 on insulin absorption after intraduodenal administration in rats (n=3±SD).
Figure 6:
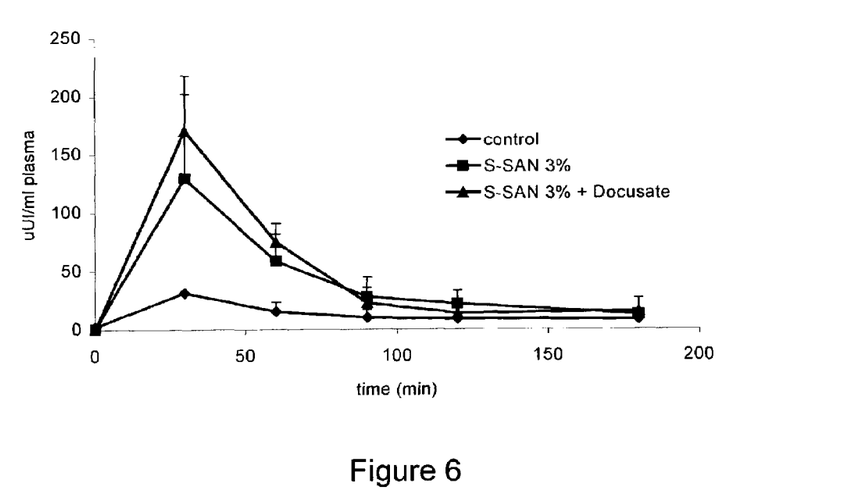
FIG. 6 is a line graph which shows the effect of S-SAN on insulin absorption after intraduodenal administration in rats (n=3±SD).

The absorption of human insulin in rats is depicted in FIGS. 5 and 6, when administered with S-NOCC60 and S-SAN, respectively, with and without sodium docusate (0.5 mg/ml). FIGS. 5 and 6 show that both S-NOCC60 and S-SAN increase the absorption of insulin significantly. FIG. 5 also shows the synergistic effect of sodium docusate on absorption when administered in combination with S-NOCC60.

This example shows that S-NOCC60 and SSAN1B increase the absorption of insulin from the small intestine and that docusate may play a synergistic role.

Thus, it is evident that the compositions of the invention can modify the permeability of the cells to allow penetration of therapeutic agents. These compositions can be used to deliver a wide variety of therapeutic agents.

The foregoing examples are merely exemplary and those skilled in the art will be able to determine other modifications to the described procedures which fall within the scope of the invention. Accordingly, the invention is defined by the following claims and equivalents thereof.

The invention claimed is:

1. A method of delivering a therapeutic agent across a membrane formed of cells selected from a group consisting of endothelial cells and epithelial cells by improving the permeability for said therapeutic agent across said membrane, comprising the step of delivering a composition including said therapeutic agent and a sulphated carboxymethylchitosan or a salt thereof as a primary carrier to said membrane, wherein said therapeutic agent is not said sulphated carboxymethylchitosan or a salt thereof; and wherein the permeability of said membrane for said therapeutic agent is improved relative to the permeability of said therapeutic agent across said membrane without the addition of said sulphated carboxymethylchitosan or a salt thereof.

2. The method of claim 1, wherein said membrane is located on a body part selected from the group consisting of the nose, oral cavity, stomach, intestine, vagina, skin and eye of a subject.

3. The method of claim 1, wherein said therapeutic agent is selected from the group consisting of proteins, peptides, nucleic acids, and fragments thereof.

4. The method of claim 3, wherein said therapeutic agent is a peptide having a molecular weight between about 700 and about 5000 daltons.

5. The method of claim 3, wherein said therapeutic agent is a protein having a molecular weight between about 5000 and about 500,000 daltons.

6. The method of claim 1, wherein said therapeutic agent has a molecular weight between about 100 and about 700 daltons.

7. The method of claim 1, wherein said therapeutic agent is a therapeutic macromolecule.

8. The method of claim 7, wherein said therapeutic macromolecule is a heparin.

9. The method of claim 1, wherein said sulphated carboxymethylchitosan or a salt thereof has a degree of sulphation of between about 0.03 and 1.0.

10. The method of claim 9, wherein said sulphated carboxymethylchitosan or a salt thereof has a degree of sulphation of between about 0.1 and about 1.0.

11. The method of claim 10, wherein said sulphated carboxymethylchitosan or a salt thereof has a degree of sulphation between about 0.1 and about 0.6.

12. The method of claim 11, wherein said sulphated carboxymethylchitosan or a salt thereof has a degree of sulphation between about 0.2 and about 0.4.

13. The method of claim 1, wherein said composition further comprises a permeation enhancer.

14. The method of claim 13, wherein said permeation enhancer comprises a surfactant.

15. The method of claim 13, wherein said permeation enhancer is selected from the group consisting of docusate sodium, docusate calcium, docusate potassium, sodium dodecyl sulfate, sodium caprylate, sodium cholate, sodium deoxycholate, sodium taurocholate, sodium glycocholate, and mixtures thereof.

16. The method of claim 15, wherein said permeation enhancer is docusate sodium.

17. The method of claim 1, wherein said composition further comprises a protecting agent.

18. The method of claim 17, wherein said protecting agent is selected from the group consisting of a protease inhibitor, a stabilizing agent, and mixtures thereof.

* * * * *